(12) United States Patent
Schajer (10) Patent No.: US 9,330,493 B2
(45) Date of Patent: May 3, 2016

(54) METHOD FOR GENERATING A 3D REPRESENTATION OF AN OBJECT

(75) Inventor: Gary Stephen Schajer, Vancouver (CA)

(73) Assignee: FPINNOVATIONS, St-Jean, Pointe-Claire, Quebec (CA)

( * ) Notice: Subject to any disclaimer, the term of this patent is extended or adjusted under 35 U.S.C. 154(b) by 243 days.

(21) Appl. No.: 13/994,522

(22) PCT Filed: Dec. 15, 2011

(86) PCT No.: PCT/CA2011/001384
§ 371 (c)(1),
(2), (4) Date: Aug. 21, 2013

(87) PCT Pub. No.: WO2012/079162
PCT Pub. Date: Jun. 21, 2012

(65) Prior Publication Data
US 2014/0146937 A1 May 29, 2014

Related U.S. Application Data

(60) Provisional application No. 61/423,268, filed on Dec. 15, 2010.

(51) Int. Cl.
*G06T 17/00* (2006.01)
*G01N 23/04* (2006.01)

(52) U.S. Cl.
CPC ............ *G06T 17/00* (2013.01); *G01N 23/046* (2013.01); *G01N 2223/419* (2013.01)

(58) Field of Classification Search
CPC ............ A61B 17/155; A61B 17/157; A61B 17/1764; A61B 19/50; A61B 2019/508; A61F 2002/30948; G06T 17/00; G01N 23/04; G01N 23/046; G01N 23/18; G01N 33/46; G01N 2223/083; G01N 2223/419; G01N 2223/601; G01N 2223/612; G01N 2223/619
See application file for complete search history.

(56) References Cited

U.S. PATENT DOCUMENTS 5,023,805 A   6/1991  Aune et al.
5,394,342 A   2/1995  Poon
(Continued)

FOREIGN PATENT DOCUMENTS

EP        0574098       12/1993
WO   WO2010034117    4/2010

OTHER PUBLICATIONS

Miller et al., Neuroimage Registration as Displacement-Zero Traction Problem of Solid Mechanics, Oct. 2006, MICCAI 206: Computational Biomechanics for Medicine, p. 8, 11.*
Shivana et al., Towards Automating Patient-specific Finite Element Model Development, Oct. 2006, MICCAI 206: Computational Biomechanics for Medicine, p. 86.*

(Continued)

*Primary Examiner* — Glen Kao
(74) *Attorney, Agent, or Firm* — Norton Rose Fulbright Canada LLP (57) ABSTRACT

There is described a method for generating a 3D representation of an object, the method comprising retrieving a 3D structure representative of the object and comprising a plurality of voxels each having a respective position therein, each one of the voxels being shaped to mimic a shape of at least a portion of a potential internal feature for the respective position; receiving a densitometry measurement comprising densitometry data of the object; assigning a density value to each one of the voxels using the received densitometry data, thereby generating a 3D model of the object; and outputting the 3D model.

15 Claims, 8 Drawing Sheets

(56) References Cited

U.S. PATENT DOCUMENTS

| | | | |
|---|---|---|---|
| 6,157,698 A * | 12/2000 | Pietikainen et al. | 378/58 |
| 6,597,761 B1 | 7/2003 | Garms, III | |
| 6,757,354 B2 | 6/2004 | Skatter et al. | |
| 6,778,681 B2 | 8/2004 | Garms et al. | |
| 6,904,123 B2 * | 6/2005 | Lang | 378/54 |
| 7,149,633 B2 | 12/2006 | Woods et al. | |
| 7,382,852 B2 | 6/2008 | Edic et al. | |
| 7,558,439 B2 | 7/2009 | Weese et al. | |
| 2004/0102688 A1 * | 5/2004 | Walker et al. | 600/407 |
| 2006/0110071 A1 * | 5/2006 | Ong et al. | 382/294 |
| 2009/0285355 A1 * | 11/2009 | Brada et al. | 378/20 |

OTHER PUBLICATIONS

Schmoldt et al. "Nondestructive Evaluation of Hardwood Logs: CT Scanning, Machine Vision and Data Utilization", published in Nondestructive Testing and Evaluation, vol. 15, pp. 279-309, 1999.

Seger and Danielsson "Scanning of logs with linear cone-beam Tomography", published in Computers and Electronics in Agriculture, vol. 41, pp. 45-62, 2003.

Kalender et al. "Spiral CT Medical Use and Potential Industrial Applications", published in SPIE vol. 3149, pp. 188-202, 1997.

International Search Report for PCT/CA2011/001384.

* cited by examiner

FIGURE 1a

PRIOR ART

METHOD FOR GENERATING A 3D REPRESENTATION OF AN OBJECT

CROSS-REFERENCE TO RELATED APPLICATIONS

This application is a National entry of PCT/CA2011/001384 filed Dec. 15, 2011, in which the United States of America was designated and elected, and which remains pending in the International phase until Jun. 15, 2013, which application in turn claims priority under 35 USC 119(e) from U.S. Provisional Application Ser. No. 61/423,268, filed Dec. 15, 2010.

FIELD OF THE INVENTION

The present application generally relates to a method, device and system for generating a 3D representation of an object.

BACKGROUND ART

The identification of the arrangement of interior features of solid objects using Computed Tomography (CT) is a well-established field, with typical applications in medicine and industrial quality control inspection. Commonly, the object of interest has a general shape, so the most general form of CT analysis must be used, with consequent requirements for very sophisticated equipment, extensive measurements and substantial mathematical calculations. In the case of objects with known patterns of overall shape and internal features ("a-priori knowledge"), significant savings can be made in equipment sophistication, number of needed measurements and size of mathematical calculation by building the a-priori knowledge into the calculation.

Log quality assessment is an important need in wood processing operations to enable informed choices to be made for subsequent log processing. A great benefit can be obtained by knowing in advance the most advantageous purpose to which each log can be put, for example, for the production of veneer, specialty woods, dimension lumber or pulp chips. In general, the best economic result is achieved by matching each log to the highest value application to which it is suited. Conversely, a great benefit can also be obtained by knowing in advance to what purposes each log cannot be put. For example, low quality logs that cannot produce useful sawn products should be diverted away from entering a sawmill, thus avoiding much redundant and costly material handling.

Log quality assessment has traditionally been done visually by skilled workers. The shape of the outside surface gives important clues to log characteristics, allowing a first rough sort of the cut logs to be made in the forest at the time of cutting. Further, mechanized inspection at the sawmill, commonly based on optical measurement of the surface shape of the logs, provides a more detailed assessment. However, it is often challenging to try to infer the interior features of a log based on surface shape measurements. Many interior features cannot be easily identified by examination of the surface, and thus go undetected.

X-ray inspection of has been introduced as a means of viewing the interior of logs. Typical systems involve making radiographs of each log, thus producing images of a log analogous to a chest X-ray image of a person. In U.S. Pat. No. 7,149,633, Woods et al. describe a procedure for inspecting sawn boards from radiographs. Such radiographs can provide much useful information about each log, but they are limited to providing 2-dimensional results. They cannot indicate the 3-dimensional character of the interior structure.

X-ray inspection from two or more directions has been introduced to provide the missing information in the third dimension. Aune and So describe such a system in U.S. Pat. No. 5,023,805, also Poon in U.S. Pat. No. 5,394,342, and Skatter in U.S. Pat. No. 6,757,354. Such systems have been only partially successful because it is very difficult to infer 3-dimensional information from radiographic measurements in a small number of directions. Typically, measurements need to be made in a large number of directions to allow 3-dimensional information to be inferred with confidence.

In an effort to enhance the capabilities of multi-directional imaging, medical style Computed Tomography (CT) has introduced for sawmill use. Schmoldt et al. summarize some typical applications in "Nondestructive Evaluation of Hardwood Logs: CT Scanning, Machine Vision and Data Utilization", published in Nondestructive Testing and Evaluation, Vol. 15, pp. 279-309, 1999. The technique involves making high-resolution X-ray measurements in a very large number of directions, possibly exceeding 1000. A typical arrangement is to rotate an X-ray source and opposing detector array around the specimen, making measurements at numerous angular steps around the rotation path. With conventional single-slice systems, all measurements during a given rotation are contained within a single cross-section. The X-ray detectors are set along a line within the plane of the cross-section. When all measurements in one cross-sectional slice are completed, the system moves on to measure the next cross-sectional slice, and so on for each slice individually.

Single-slice CT systems tend to be relatively slow because they measure only one slice at a time. In addition, they make very inefficient use of the X-ray beam because they use only a small part of it along a narrow line. As described by Seger and Danielsson in "Scanning of logs with linear cone-beam Tomography", published in Computers and Electronics in Agriculture, Vol. 41, pp. 45-62, 2003, greater use of the X-ray beam can be made by installing additional X-ray detectors along rows parallel to the central row. They provide additional measurements that can improve the stability of the resulting reconstructions.

The need to make measurements in separate steps at discrete cross-sections along the length of the measured object makes the slice-by-slice style of CT measurement inconvenient for industrial use with logs. An alternative approach is to make measurements while the X-ray source and detector array follow a continuous spiral path around the specimen. Such systems are now well developed for medical applications, as described by Kalender et al. in "Spiral CT Medical Use and Potential Industrial Applications", published in SPIE Vol. 3149, pp. 188-202, 1997. Garms describes an industrial application in U.S. Pat. No. 6,778,681.

CT measurements require that the relative motions of the scanner and the measured object are very precise and well defined, else artefacts are created in the CT reconstruction. Such accurate relative motions are achieved in medical scanners by rotating the X-ray source and detectors within large mechanical bearings while advancing the patient along a precise linear path. This is a very complex and costly arrangement. Several approaches have been developed to reduce reconstruction artefacts, for example, as described by Edic in U.S. Pat. No. 7,382,852, and Weese in U.S. Pat. No. 7,558,439, but accurate relative motions are still needed.

In U.S. Pat. No. 6,157,698, Pietikainen and Alisto describe the use sector-shaped voxels with annular boundaries indicated at equal radial intervals. This use of voxels with greatly dissimilar volumes gives poor results for the small interior voxels. The disclosed procedure uses planar cross-sections, and thus extensive post-processing of the reconstruction results is required to identify knots. In addition, the focus is on knot identification, without consideration of the use of annular voxels without sector division as a means for identifying axisymmetric features.

In U.S. Pat. No. 6,597,761, Garms describes the use of cylindrical projections for log evaluation. This process provides a post-processing step to assist interpretation of the results of a conventional CT measurement using many small rectangular voxels. Thus, all the requirements of conventional CT measurements must still be met, for example, many fine-resolution measurements, maintenance of very accurate relative motions, and very large computational effort. By defining the voxel arrangement as described herein, all these requirements may be relaxed significantly, and a much more efficient and economical CT measurement can be achieved.

Even with all these developments, it remains very challenging to try to implement CT methodology for practical industrial use. Such applications cannot tolerate the high cost, complexity and modest speed that are acceptable in medical systems. What is required is an industrial system of moderate cost and complexity, and of sufficient speed to make measurements in "real-time", so that it can keep up with product flow without causing delay. Therefore, there is a need for achieving these objectives by making and using the measured X-ray data in a much more effective way.

SUMMARY

In accordance with a first aspect of the invention, there is provided a method for generating a 3D representation of an object, the method comprising: retrieving a 3D structure representative of the object and comprising a plurality of voxels each having a respective position therein, each one of the voxels being shaped and sized to mimic a shape of at least a portion of a potential internal feature for the respective position; receiving a densitometry measurement comprising densitometry data of the object; assigning a density value to each one of the voxels using the densitometry data, thereby generating a 3D model of the object; and outputting the 3D model.

In accordance with another aspect of the method herein described, further comprising generating the 3D structure comprising the voxels.

In accordance with yet another aspect of the method herein described, further comprising displaying the 3D model.

In accordance with still another aspect of the method herein described, the respective position of the voxels is made at equal intervals of an angular position of the object.

In accordance with yet still another aspect of the method herein described, the densitometry measurement is obtained using an X-ray source and one or more detectors for capturing X-radiation from the source.

In accordance with a further aspect of the method herein described, the X-ray source is a cone-beam.

In accordance with yet a further aspect of the method herein described, the densitometry measurement for the object is carried out while creating a spiral motion of the object as the object is moved through the X-ray source and detector.

In accordance with another aspect of the invention, there is provided a device for generating a 3D representation of an object, the device comprising: a memory for storing a 3D structure representative of the object and comprising a plurality of voxels each having a respective position therein, each one of the voxels being shaped and sized to mimic a shape of at least a portion of a potential internal feature for the respective position; a communication unit for receiving a densitometry measurement comprising densitometry data of the object; a processing unit configured for assigning a density value to each one of the voxels using the densitometry data in order to generate a 3D model of the object; and outputting the 3D model via the communication unit.

In accordance with still a further aspect of the device herein described, the processing unit is further configured for generating the 3D structure comprising the voxels.

In accordance with yet still a further aspect of the device herein described, further comprising a display for displaying the 3D model.

In accordance with the device herein described, the processing unit is adapted for voxel scaling for computation and economy.

In accordance with the device herein described, the processing unit compensates for transverse motions of the measured object for computation and economy.

In accordance with another aspect of the invention, there is provided a system for generating a 3D representation of an object, the system comprising: an imaging device for sensing the object and generating a densitometry measurement comprising densitometry data of the object; a 3D model generator comprising a memory for storing a 3D structure representative of the object and comprising a plurality of voxels each having a respective position therein, each one of the voxels being shaped and sized to mimic a shape of at least a portion of a potential internal feature for the respective position; a processing unit for assigning a density value to each one of the voxels using the densitometry data in order to generate a 3D model of the object; and a display unit for displaying the 3D model.

In accordance with one aspect of the system herein described, the densitometry measurement is obtained with an X-ray source and a detector capturing the X-ray source.

In accordance with another aspect of the system herein described, the X-ray source is a cone-beam configuration.

In accordance with yet another aspect of the system herein described, further comprising a multi-source system of X-ray source cone-beams.

In accordance with still another aspect of the system herein described, the X-ray detectors are arranged over an extended area opposite the X-ray source and the object.

The term "3D structure" should be understood as any empty 3D surface of an object to be represented, parceled to form a plurality of voxels.

The term "3D model" should be understood as a 3D structure of an object to be represented in which a density value has been assigned to each one of the voxels using densitometry measurement where this measurement comprises densitometry data of the object to be represented.

DETAILED DESCRIPTION OF PARTICULAR EMBODIMENTS

The present invention provides a CT method for identifying interior features of cylindrical objects that greatly guides and stabilizes the required calculations, enables useful results to be achieved with far fewer measurements than would be required for conventional CT scanning, and is tolerant of imperfections of the relative motion of the measured object. The method involves making radiation attenuation measurements at multiple locations and along multiple paths during relative movement of the measured object and sensors. The measured data are then used as the basis of a Computed Tomography (CT) calculation to estimate the spatial arrangement of the interior features of the object.

An example cylindrical object could be a log. For a log, of particular interest are the locations and sizes of the knots, the location of the heartwood/sapwood boundary, and the possible locations of rot and compression wood. The central idea of the invention is to use a-priori information to guide the CT calculations. For logs, this information includes the knowledge that logs are generally cylindrical, that features such as heartwood/sapwood and rot are generally axisymmetric, and that knots are aligned radially and at specific angles to the log central axis.

These physical characteristics are built into the CT calculations by replacing the brick-shaped voxels conventionally used in CT work by voxels whose boundaries are based on a cylindrical coordinate system. The matching of the voxel shapes with the feature shapes enables the features to be well represented by fewer, larger voxels. This arrangement greatly reduces the amount of data that need be collected and the size of the subsequent mathematical reconstruction of the log structure.

These calculations are formulated here in scaled form to allow significant economies in the formulation and solution of the reconstruction. This feature also allows the calculations to be done such that their sensitivities to log ellipticity and imperfections in log relative motions are much reduced. The reduction in sensitivity to relative motion imperfections is particularly significant because it greatly simplifies the required mechanical arrangement of the CT scanner and measured object, making it feasible to keep the X-ray source and detectors stationary and moving only the measured object. Such an arrangement has previously not been feasible with logs because of their large size and irregular shape.

To simplify the presentation, the following description refers to densitometry measurements data made using X-rays but it is understood that another radiation source such as beta rays and gamma rays could also be used, according to the needs of the application. This method applies equally to the use of any form of radiation. Similarly, the description refers to configurations where the X-ray source(s) and detectors remain stationary and that the measured object moves. This is the preferred arrangement here because practical X-ray sources and detectors are complex and delicate components, and are much more easily and reliably operated in fixed positions.

This method does not require very high precision motions, thereby allowing the more straightforward arrangement of translating (and rotating as needed) the measured object through the X-ray scanner. This fixed arrangement differs from the standard configuration used in medical applications, where the X-ray source(s) and detectors rotate around the patient. It is to be understood that the following description applies equally to the use of moving X-ray source(s) and detectors with equivalent motion relative to the measured object.

The present method is general and can be applied to many different types of objects. To illustrate the practicality of the invention, the description is expressed in terms of a specific practical application, the inspection of logs. However, it is to be understood that the inventive ideas described for use with logs equally apply for use with other objects.

Figure 1A:
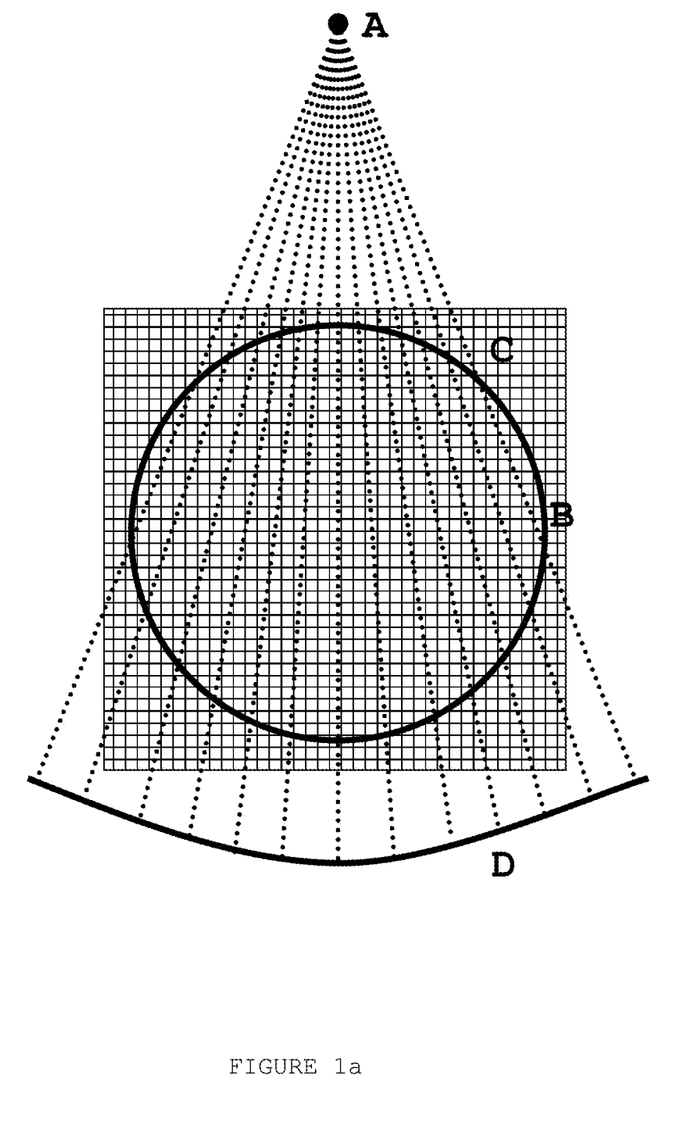
FIG. 1a illustrates a configuration for general single-plane CT density measurements using rectangular voxels in accordance with to prior art.

FIG. 1a schematically shows a prior art basic sensor arrangement for single-plane CT measurements. A fan beam from an X-ray source emitting X-radiation. A passes through the measured object B, here a log. The local parts of the beam are attenuated according to the line integrals of the material density along and various paths shown, and are individually measured by the sensors within the detector array D. Conventional CT scanning divides the cross-sectional area to be evaluated into a rectangular grid of voxels C, as shown in FIG. 1a.

The measured object rotates relative to the X-ray source and detectors, enabling the measurement of many sets of attenuation measurements, the projections, to be made over a wide range of measurement directions. In a preferred embodiment there may be more than one X-ray source and detector. In an alternative embodiment, there may be one X-ray source and one or more detectors. The data from the projections can then be used to evaluate the local material density within each of the voxels shown in FIG. 1a using any of several established algorithms, for example, Filtered Back Projection, Algebraic Reconstruction Technique, Fourier Slice Theorem, etc.

The rectangular arrangement of voxels shown in FIG. 1a is advantageous in typical applications where the measured object has general features not confined a specific pattern. The rectangular grid of voxels provides a flexible way to work with and present such general results. However, the price of this generality is that many projections, very detailed and accurate measurements, and substantial computations are required to give satisfactory results. The resulting high cost, complexity and modest speed of equipment using this approach seriously impede its use for industrial scanning of cylindrical objects.

In the particular case of log scanning, a different approach can be taken. Logs have a strongly defined cylindrical shape with prominent axisymmetric features such as outer surface and heartwood/sapwood boundary. In addition, defects such as rot also often have axisymmetric geometry. For identification of such features, great measurement and computational economy can be achieved by doing the CT reconstruction using voxels that are arranged in a pattern that mirrors the features of interest.

Figure 1B:
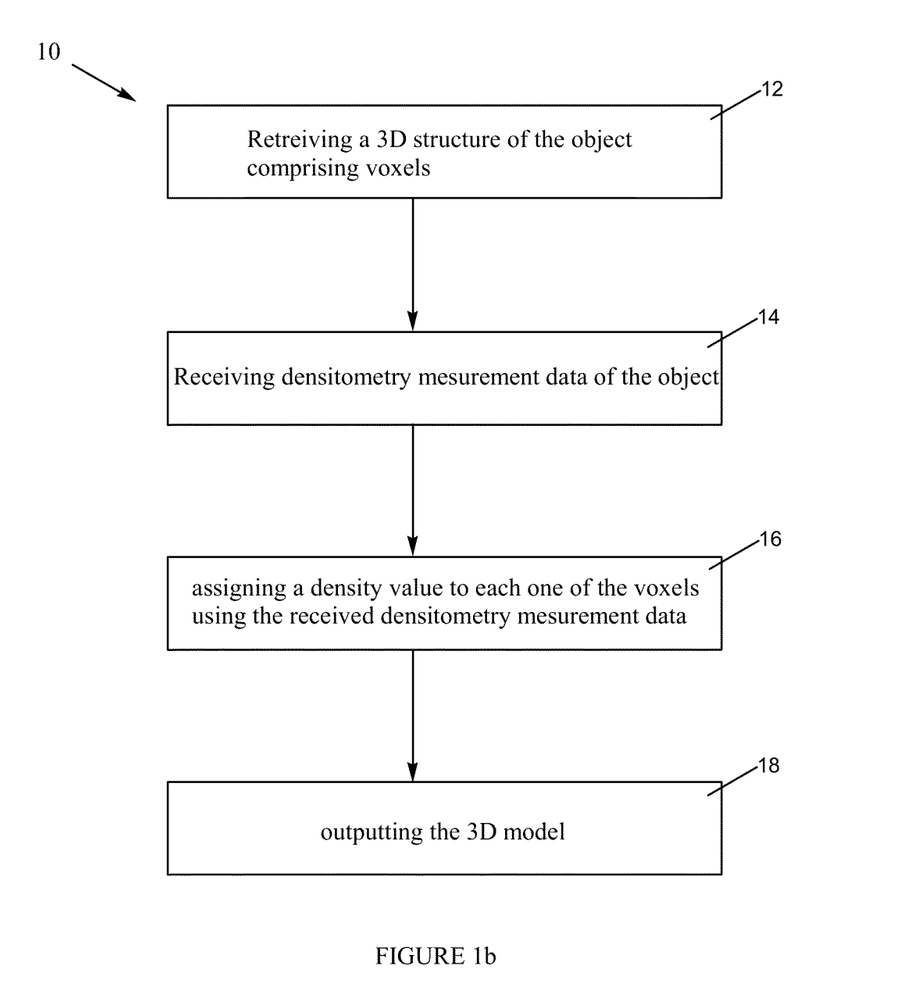
FIG. 1b is a flow chart of a method for generating a 3D representation of an object, in accordance with an embodiment.

In one embodiment, the method for generating of a 3D representation of an object 10 as shown in a flow chart of FIG. 1b comprises four steps. The first step 12 is retrieving a 3D structure representative of the object and comprising a plurality of voxels each having a respective position therein, each one of the voxels being shaped to mimic a shape of at least a portion of a potential internal feature for the respective position, the voxels are spatially referenced relative to the object. The second step 14 is receiving a densitometry measurement of the object where this measurement comprises densitometry data. The third step 16 is assigning a density value to each one of the voxels using the received densitometry data and the final step is thereby generating a 3D model of the object and the final step is outputting the 3D model. The voxels mimic the features in shape, size and location.

Figure 1C:
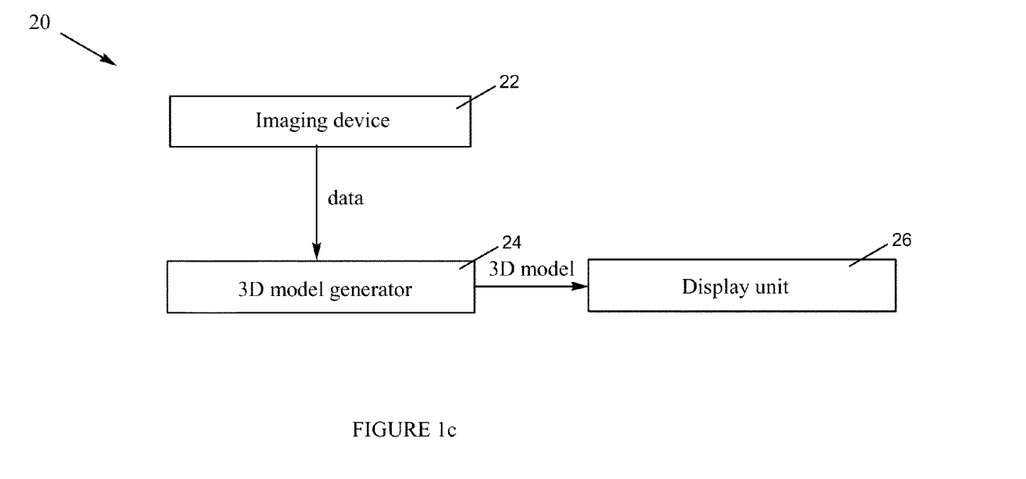
FIG. 1c is a flow chart of a system for generating a 3D representation of an object, in accordance with an embodiment.

In another embodiment, the system for generating of a 3D representation of an object 20 as shown in a flow chart of FIG. 1c comprises three elements. The first element is an imaging device 22 for sensing the object and generating a densitometry measurement comprising densitometry data of the object. The second element is a 3D model generator 24 comprising a memory for storing a 3D structure representative of the object and comprising a plurality of voxels each having a respective position therein, each one of the voxels being shaped to mimic a shape of at least a portion of a potential internal feature for the respective position; thus, here too each voxel is spatially referenced relative to the object. The 3D model generator also comprises a processing unit for assigning a density value to each one of the voxels using the received densitometry data in order to generate a 3D model of the object. The third element is a display unit 26 for displaying the 3D model. The processing unit is adapted to compensate for transverse motions of the measured object. Therefore, the object does not need to be rotated about its exact axis. The device's processing unit will accommodate transverse motion of the object being scanned, this affords the device both computational efficiency and economy, that favourably impact the cost of the device.

Figure 2:
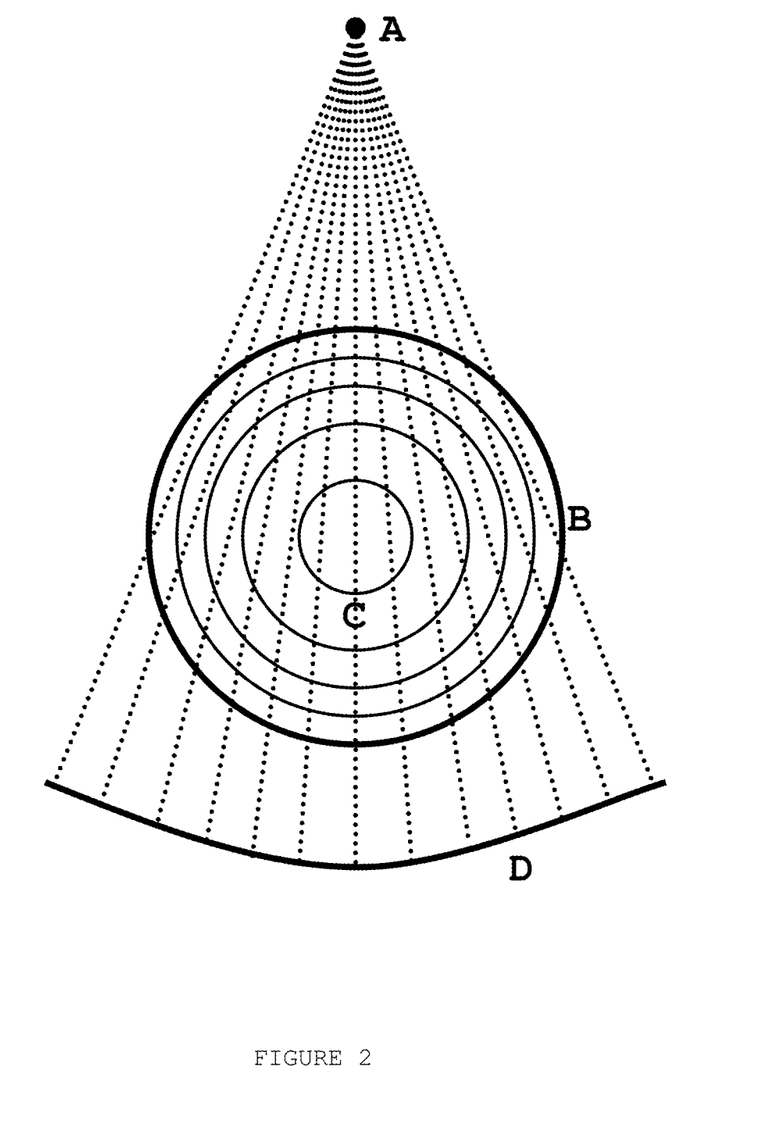
FIG. 2 illustrates a voxel arrangement for axisymmetric single-plane density measurements of the object in cross-section, in accordance with an embodiment.

FIG. 2 shows an annular arrangement of voxels designed for axisymmetric reconstructions. The axisymmetric character of the reconstruction is built into the voxel arrangement, thereby automatically incorporating this a-priori information about the measured object. This inclusion of a-priori information reduces the dimensionality of the voxels from a 2-dimensional arrangement in FIG. 1a to a 1-dimensional arrangement in FIG. 2. Therefore, in a preferred embodiment the voxels are annular cylinders, aligned with the axis of the object.

The resulting reduction in the number of voxels to be evaluated greatly reduces and stabilizes the calculations required for the CT reconstruction, and enhances the industrial practicality of the measurement. Computational stability is further enhanced if the boundary radii are chosen such that the voxels have approximately equal volumes, allowing similar fractional interaction with the X-ray beam. This effect can be achieved by choosing the boundary radii in approximately equal steps of the square of the radius.

Identification of knots in logs requires a different voxel pattern. Knots are the roots of the branches of a tree. They initiate at the centerline of the tree and grow radially outward, enlarging in their diameter with increase in radius within the tree trunk. The arrangement of voxels shown FIG. 3 mirrors this geometry, where a sector could contain a knot. As with the annular arrangement of voxels in FIG. 2, the inclusion of a-priori information about the expected shape of knots in FIG. 3 reduces the dimensionality and the total number of voxels to be evaluated, thereby greatly reducing and stabilizing the calculations required for the CT reconstruction, and enhancing the industrial practicality of the measurement. Computational stability is further enhanced if the sector angles are chosen to be all the same, thereby creating voxels with similar volumes, or substantially equal volumes.

Figure 3:
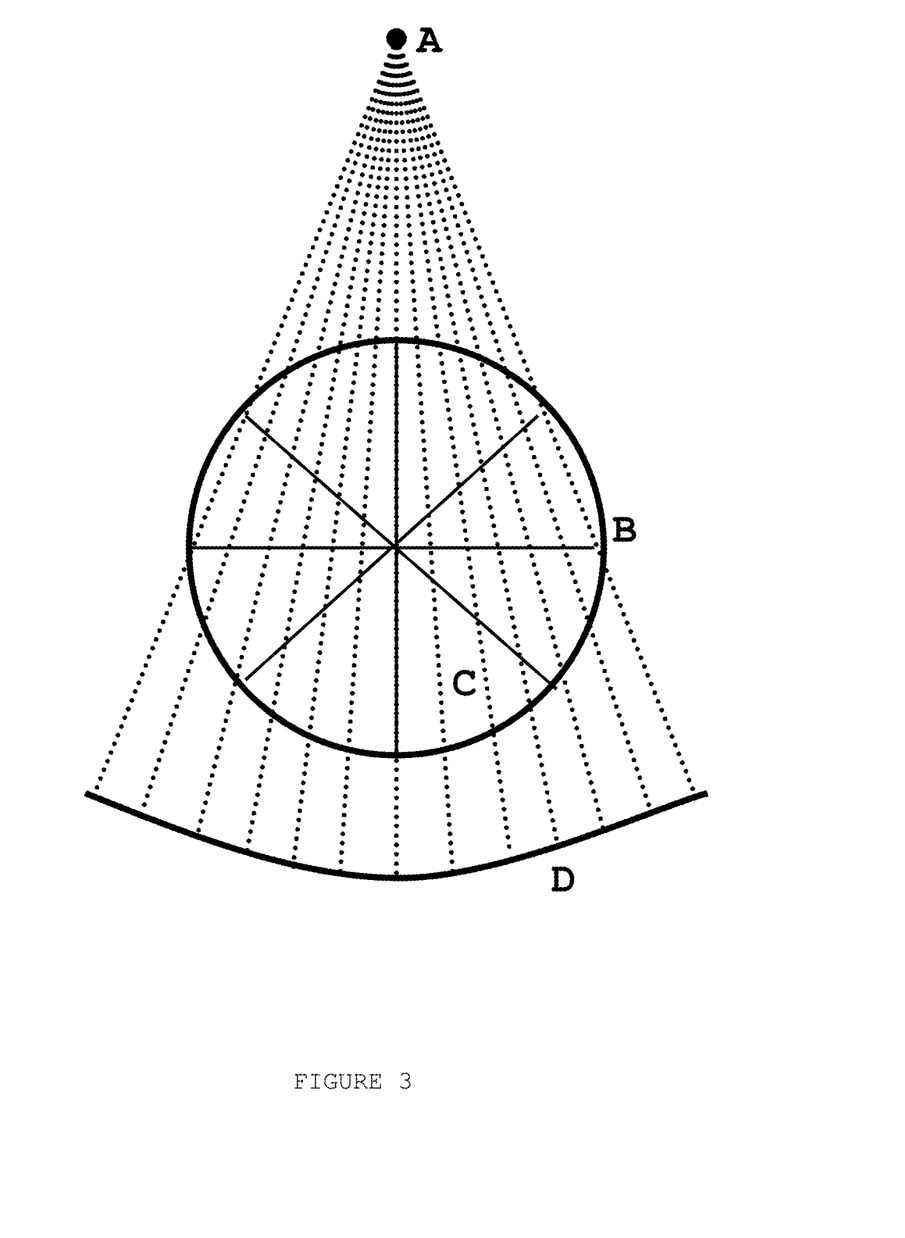
FIG. 3 illustrates an voxel arrangement for angular single-plane density measurements of the object in cross-section, in accordance with an embodiment.

FIG. 2 and FIG. 3 define the radial and angular boundaries of voxel geometries that embody a-priori information about the internal structure of logs. The conventional choice for the axial boundary is a plane cross-sectional surface. This choice can be used. However, greater contrast can be achieved by using an axial boundary that embodies further a-priori information about the log internal structure.

In most tree species, the branches grow from the tree centerline at a characteristic angle, most often slightly upward in the standing tree. This angle is known for the log species being scanned. To accommodate this knot geometry, the axial surface of the voxels can be chosen to be slightly conical, as in FIG. 4, with a cone angle to match the knot growth angle. Consequently, the knots will tend to appear within a single conical cross-section rather than being distributed across several adjacent planar cross-sections.

This feature greatly increases image contrast and knot resolution capability. Other non-planar surface shapes such as a paraboloid and a spherical cap also provide reasonable representations of knot shape that could be used in place of a cone should they prove mathematically more convenient for a chosen reconstruction algorithm.

When choosing a voxel pattern for a given application, the three boundary arrangements can be used individually or combined as desired. For example, when it is desired to identify the heartwood/sapwood boundary, the voxel arrangement shown in FIG. 2 could be used alone. No sectors are required and it is not necessary to use non-planar cross-sections. Alternatively, when it is desired to identify full-length knots, a voxel arrangement combining FIG. 3 and FIG. 4 could be used.

Figure 4:
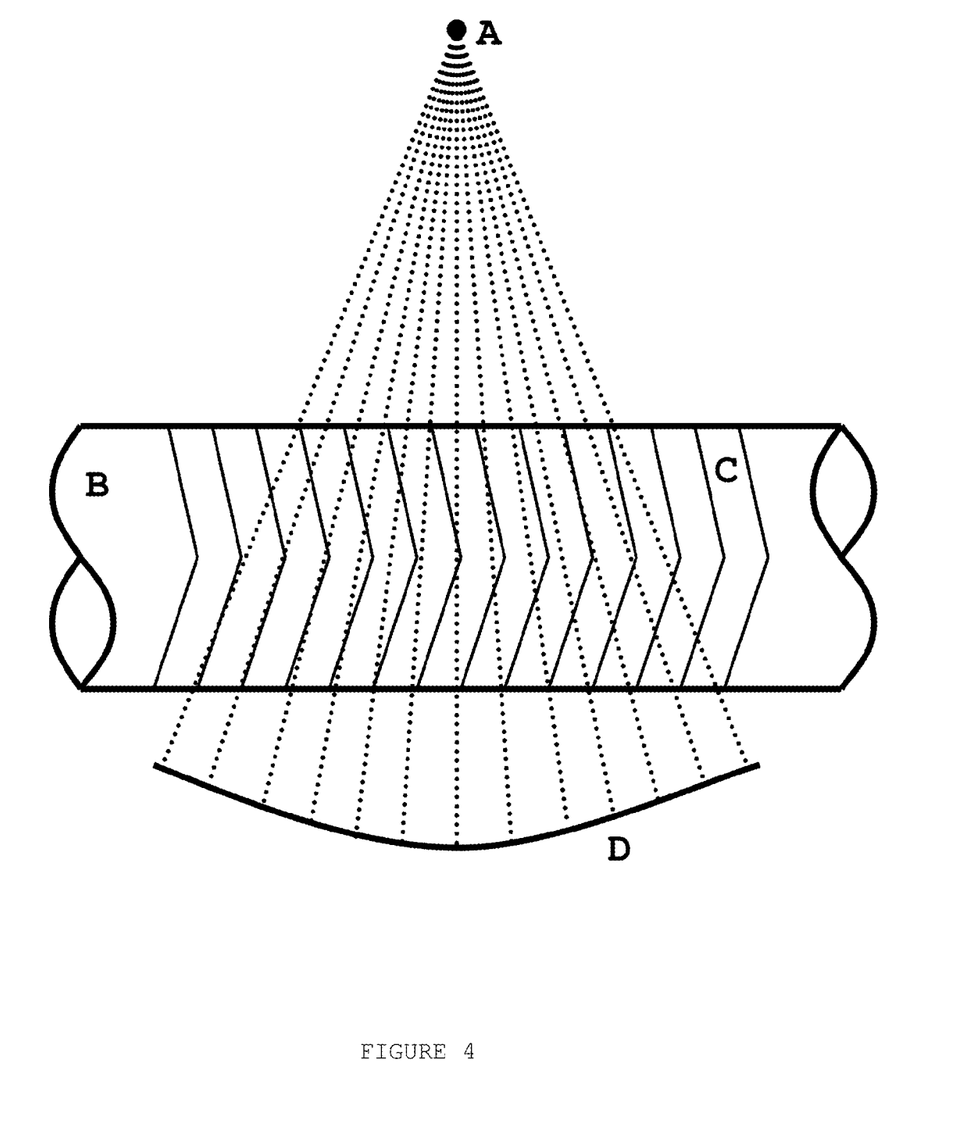
FIG. 4 illustrates a voxel arrangement for single-plane density measurements length of the object, in accordance with an embodiment.

In addition, if it were also desired to distinguish partial length knots from full-length knots, a voxel arrangement combining FIG. 2, FIG. 3 and FIG. 4 could be used. When multiple identification objectives exist simultaneously, separate calculations can be done for each chosen voxel pattern using the same measured data.

An important common feature of the various voxel arrangements shown in FIG. 2, FIG. 3 and FIG. 4 is that they are spatially referenced to the measured object. This differs from conventional CT practice where the voxels are fixed in space relative to the X-ray system. This feature is significant because it can remove the requirement to locate the measured object precisely within the measurement space, thereby greatly simplifying and reducing the cost of the material handling system.

Many possible algorithms can be used for reconstructing the voxel densities from the measured X-ray attenuation data. The attenuation along a given part of the X-ray beam that reaches a given detector depends on the line integral of the density of all the material that lies along the path of that part of the X-ray beam that reaches a given detector.

For a monochromatic beam, Beer's Law applies:

$$a = -\ln\left(\frac{I}{I_0}\right) = \int \beta \rho \, ds \qquad (1)$$

where a is the local attenuation of the X-ray beam, $I_0$ is the local beam intensity with no log present, I is the local beam intensity with the log in place, $\beta$ is the mass attenuation coefficient, and $\rho$ is the local material density at distance s along the given X-ray line. The mathematical expression of the second term of Eq. (1) differs in detail for a polychromatic source such as an X-ray tube, but the integral form of the third term is retained.

A given X-ray line in any of the voxel arrangements shown in FIG. 1a, FIG. 2, FIG. 3 or FIG. 4, may pass through one or more voxels. If it is assumed that the material density is constant within a given voxel, then Eq. (1) can be expressed as $$a = \beta \Sigma \rho_j s_j \quad (2)$$

where $\beta$ is the mass attenuation coefficient, $\rho_j$ is the density of voxel "j", and $s_j$ is the path length within that voxel.

The attenuation measurements from many detectors can be combined as a group and expressed in matrix notation as:

$$\beta G \, d = a \quad (3)$$

where $\beta$ is the mass attenuation coefficient, G is a matrix whose elements $G_{ij}$ contain the path lengths within voxels "j" traversed by the X-ray beam reaching detector "i". a is a vector whose elements $a_i$ contain the attenuation measured at each detector "i", and d is a vector whose elements $d_j$ contain the density assigned to each voxel "j". In general, G is a very large and sparse matrix. Several practical ways have been developed for evaluating the voxel densities d, for example, by back-projection or by Fourier transformation. For the reduced number of voxels used in the present invention, direct solution of Eq. (3) could also be a practical choice. Any effective method for solving for d meets the objectives of this invention, and lies within its scope.

Figure 5:
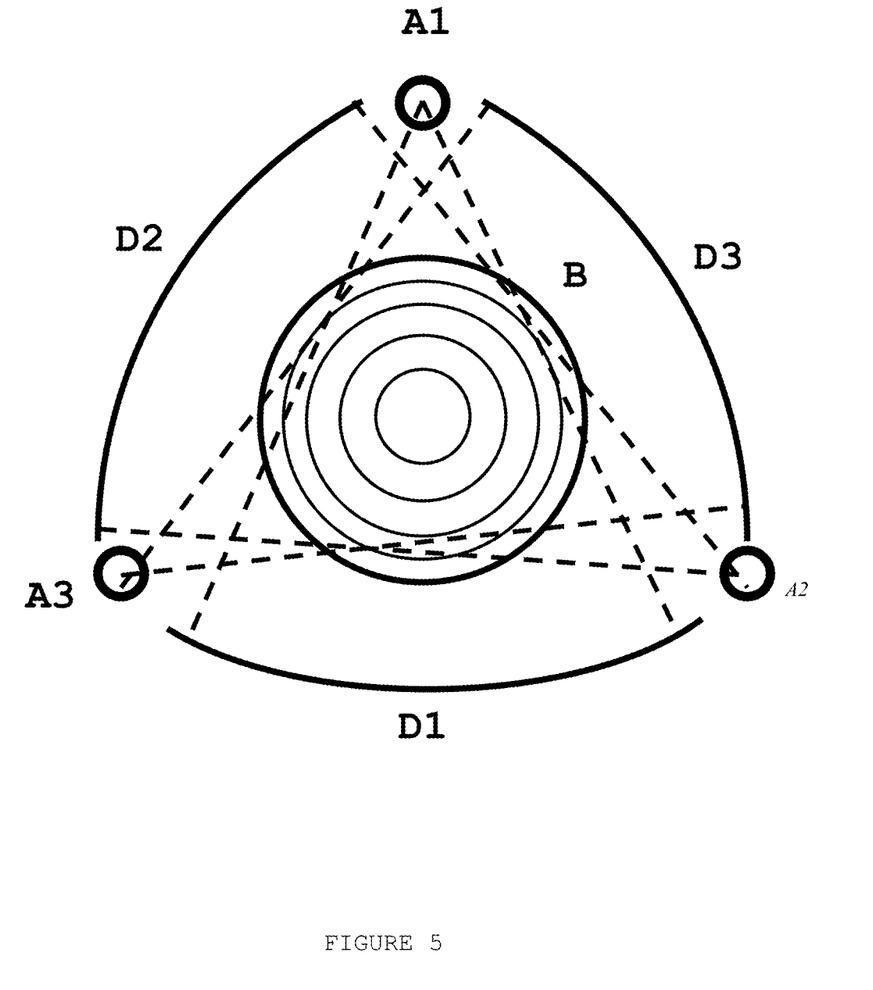
FIG. 5 illustrates a configuration using three X-ray sources and detector arrays of the object in cross-section, in accordance with an embodiment.

In practical cases, there are many more attenuation measurements than there are voxel densities to be evaluated. Equation (3) is over-determined, so a "best-fit" solution is desired. Under these conditions, reconstruction of the annular voxel arrangement in FIG. 2 could theoretically be done using a single projection. However, such a reconstruction is easily distorted by the presence of any non-axisymmetric features such as knots. Much more stable results are achieved by making and combining measurements from several directions. For example, FIG. 5 illustrates X-ray measurements made in three directions. Measurements in multiple directions have been described previously, for example, by Aune and So in U.S. Pat. No. 5,023,805, and by Poon in U.S. Pat. No. 5,394,342. This configuration is useful when working with the sector shaped voxel pattern illustrated in FIG. 3 because, in this case, a single projection does not contain sufficient information to enable a successful reconstruction.

The measurement arrangement shown in FIG. 5 is attractive because it allows the X-ray sources and detectors to remain stationary. This is a significant advantage over conventional medical CT systems, where great complexity and cost are incurred to accommodate X-ray source and detector motion. However, the use of multiple X-ray sources is also costly, and it is desirable to minimize their number.

Figure 6:
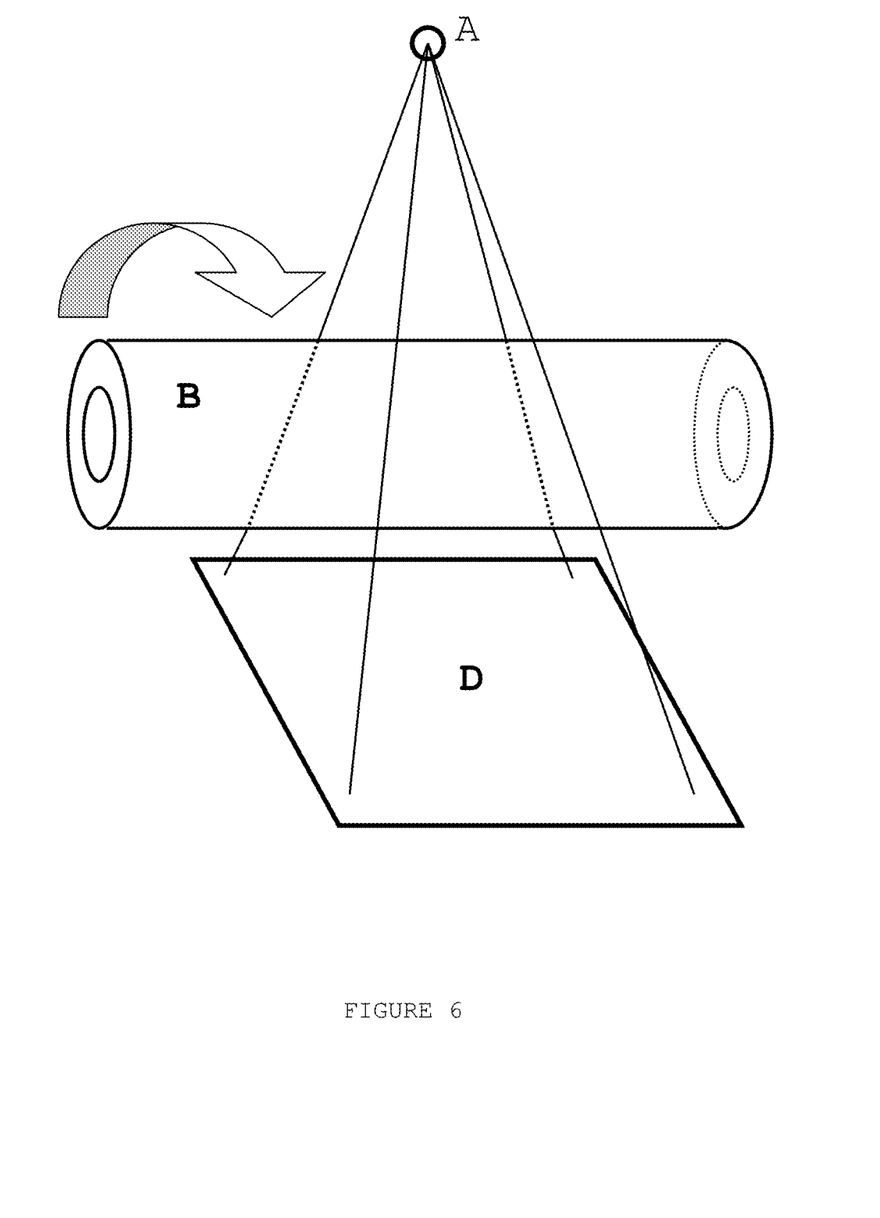
FIG. 6 illustrates a perspective schematic view of a configuration using a cone-beam X-ray source and a detector array distributed over an extended area, in accordance with an embodiment.

In addition, the highly collimated measurements made along single lines provide a limited slice of data from a tiny fraction of the available X-ray energy. This latter limitation can be ameliorated by arranging the X-ray detectors along multiple parallel lines, or over one or more extended areas, as in FIG. 6. The latter "cone-beam" arrangement uses a much greater fraction of the available X-ray radiation and provides a much richer data source. Measurements along the angled X-ray paths also assist the reconstructions with the non-planar sectors shown in FIG. 4.

In addition, it is advantageous to create a spiral motion by rotating the log around its central axis as it moves forward because this allows a single X-ray source/detector system to measure the log over a full range of projection angles. Further adaptations, such as using more than one cone-beam X-ray source/detector system can also be useful. For example, Seger and Danielsson describe a two-axis cone-beam system with linear-moving (non-spiraling) logs in "Scanning of logs with linear cone-beam Tomography", published in Computers and Electronics in Agriculture, Vol. 41, pp. 45-62, 2003.

When working with the voxel arrangements shown in FIG. 2 and FIG. 3, it is necessary to get reliable estimates of the diameter or radius of the log. This could be done by searching for the edge voxels, as is described by Skatter in U.S. Pat. No. 6,757,354. However, this method may not be reliable because the edge voxels are greatly influenced by local irregularities at the log surface. A more stable estimate of log radius can be found by assuming that the log has a circular cross-section and is of uniform density. The density profile is therefore semi-elliptical, similarly the measured attenuation profile.

By computing the position of the centroid of the attenuation profile, the center and radius of the log image can be estimated (for uniformly spaced detectors) using:

$$\text{center}, \; C = \frac{\sum k a_k}{\sum a_k} \quad (4)$$

$$\text{radius}, \; R = \frac{16 \left( \sum a_k \right)^2}{3 \pi^2 \sum a_k^2} \quad (5)$$

where k are the index numbers of the detectors, and $a_k$ are the corresponding attenuations.

Although not an essential feature, having X-ray detectors at uniform angular spacing allows some convenient mathematical simplifications. It is common for single-line detectors to be placed along an arc of a circle whose center is the focal point of the X-ray source. This arrangement automatically provides uniform angular spacing of the detectors. However, cone-beam systems that use modern flat-panel detectors provide uniform linear spacing rather than uniform angular spacing. The coarse spatial resolution sufficient for this invention allows the use of a convenient method to convert uniform linear detector spacing into uniform angular spacing.

The method involves controlling the way in which "binning" is done to convert the large number of finely spaced pixels that are measured by flat-panel detectors into a much smaller number of more coarsely spaced pixels. In conventional applications, both row and column binning are simultaneously done in hardware, and just the binned data are output. This process decreases the spatial resolution while increasing frame speed, compacting the data size and reducing measurement noise. However, the binned pixels remain linearly spaced.

An alternative procedure is to note that the increase in frame speed depends only on row binning, but not on column binning. Thus, if the flat-panel detector is oriented such that the rows align with the longitudinal axis, the increase in frame speed can be achieved by longitudinal pixel binning only, while retaining the original fine pixel resolution across the log diameter. Binning in the diametral direction can then be done in software using bin sizes that are smaller in the center of the panel, growing larger towards the edges such that the resulting binned pixels have uniform angular spacing.

Uniform angular detector spacing and reliable evaluation of the center and diameter of the log image open up a very important feature of the use of the voxel patterns in FIG. 2, FIG. 3 and FIG. 4. Bulk motions of the log parallel to the detector array can be entirely compensated by using a detector numbering scheme based on the center of the measured density profile instead of the geometrical center of the detector array. Bulk motions of the log perpendicular to the detector array can be mostly (but not perfectly) compensated by scaling the measured density profile according to the diameter. This latter scaling also compensates for any elliptical shape of a practical log cross-section. A direct way of doing the scaling is to take the row-binned data, use Eq. (4) and (5) to estimate the center and radius of the log image, and complete the column binning in software using only the pixels contained within the (non-zero) log image. Thus, the binned data exactly fit the log, independent of its size, bulk motions or ellipticity.

The bin boundaries are:

$$\theta_A = a\sin\left(\frac{(C-R-h)\delta}{H}\right) \quad (6)$$

$$\theta_B = a\sin\left(\frac{(C+R-h)\delta}{H}\right) \quad (7)$$

$$k = h + \frac{H}{\delta}\sin\left(\frac{(n-i)\theta_A + i\theta_B}{n}\right) \quad (8)$$

where k is the row number on the detector panel corresponding to the upper boundary of bin i, i is the index number of the bins, n is the total number of bins in a row, h is the row number on the detector panel that is perpendicular to the X-ray focus, H is the perpendicular distance from the X-ray focus to the panel, δ is the width of each row on the detector panel, and $\theta_A$ and $\theta_B$ are the boundary angles of the log image. This scaling, which fits the data and the voxels into the measured object, fundamentally differs from the conventional CT practice of fitting the data and voxels within a fixed spatial pattern. If desired, Equations (6), (7) and (8) can also be applied to the entire measured row by setting C equal to the center of the row, and R equal to its half-length.

Voxel scaling also permits a significant computational economy to be made in the formulation of matrix G in Eq. (3). This matrix contains the path lengths spanned by the various X-ray paths through the various voxels. This calculation can be time consuming. However, the voxel scaling allows the matrix to be computed once and then stored in a look-up table. The size of the look-up table can be minimized by requiring that X-ray measurements be made for log angular positions synchronized to the sector pattern shown in FIG. 3.

This feature requires that the measurements be made at equal intervals of log angular position rather than at equal intervals of time, as is conventionally done. The required triggering of measurements can be provided by a rotation measurement device such as a rotary encoder or other sensor, and allows acquisition of useful measurements even if the log speed is not uniform. This feature further reduces that requirement for accurate relative motion between scanner and measured object.

Compensation for log bulk motions allows the log scanner described here to require much less mechanical precision than conventional CT scanners. The latter are much more demanding; they must be operated very precisely so as to maintain accurate spatial registration between the specimen and the X-ray source/detector system. This is a major reason why the X-ray source/detector is conventionally rotated around the specimen. However, the source/detector system is very delicate and sensitive, and so rotating it is difficult and costly. A significant advantage of this invention is that it allows the X-ray source/detector system to remain stationary while tolerating significant imperfections in the relative motion of the measured log.

It is apparent that the inventive principles that constitute this invention can be applied to a wide range of CT measurement configurations. For example, the log could translate through single or multi-source systems exemplified by FIG. 2 and FIG. 5, where in FIG. 5 the multi-source (i.e. X-rays) are oriented around the axis of the object. The X-ray detectors could be arranged along single or multiple lines, or they could be arranged over one or more extended areas, as in FIG. 6. The latter "cone-beam" arrangement is advantageous because it takes advantage of a much greater fraction of the available X-ray radiation, provides a much richer data source, and allows much greater scanning speed. Measurements along the angled X-ray paths also assist the reconstructions with the non-planar sectors shown in FIG. 4. In addition, it is advantageous to create a spiral motion by rotating the log around its central axis as it moves forward because this allows a single X-ray source/detector system to measure the log over a full range of projection angles. Further adaptations, such as using more than one cone-beam X-ray source/detector system are also useful.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and as may be applied to the essential features hereinbefore set forth, and as follows in the scope of the appended claims. Therefore, it is understood that the method is general and is not limited to log or cylindrical object but can be also applied to many different types of objects.

The invention claimed is:

1. A method for generating a 3D model of a log having an axial center line, the method comprising:
    sensing the log with an X-ray imaging device;
    generating a densitometry measurement comprising densitometry data of the log;
    retrieving a 3D structure representative of the log and comprising a plurality of voxels each having a respective position therein, the voxels being shaped and sized to mimic a shape of at least a portion of a potential internal feature for the respective position;
    assigning a density value to each one of the voxels using the densitometry data, thereby generating the 3D model of the log;
    compensating for transverse motions from sensing of the log,
    outputting the 3D model, and
    further comprising displaying the 3D model,
wherein the potential internal feature is an annular feature and/or a knot, wherein the knot extends outward from the axial center line of the log.

2. The method according to claim 1, further comprising generating the 3D structure comprising the voxels.

3. The method according to claim 1, wherein the respective position of the voxels is made at equal intervals of an angular position of the log.

4. The method according to claim 1, wherein the densitometry measurement is obtained using an X-ray source and one or more detectors for capturing X-radiation from the source.

5. The method according to claim 4, wherein the X-ray source is a cone-beam configuration.

6. The method according to claim 5, wherein the generating the densitometry measurement for the log is carried out while creating a spiral motion of the log as the log is moved through the X-ray source and detector.

7. A device for generating a 3D model of a log, the device comprising:
   a memory storing a 3D structure representative of the log having an axial center line and comprising a plurality of voxels each having a respective position therein, the voxels being shaped and sized to mimic a shape of at least a portion of a potential internal feature for the respective position;
   a communication unit configured to receive a densitometry measurement comprising densitometry data of the log from an X-ray sensing of the log; and
   a processing unit configured to assign a density value to each one of the voxels using the densitometry data in order to generate the 3D model of the log;
   wherein the 3D model is outputted via the communication unit,
wherein the potential internal feature is an annular feature and/or a knot, wherein the knot extends outward from the axial center line of the log;
wherein the processing unit compensates for transverse motions of the sensing of the log.

8. The device according to claim 7, wherein the processing unit is further configured to generate the 3D structure comprising the voxels.

9. The device according to claim 8, further comprising a display for displaying the 3D model.

10. The device according to claim 9, wherein the processing unit is adapted for voxel scaling.

11. A system for generating a 3D model of a log having an axial center line, the system comprising:
   an imaging device configured to sense the log and generate a densitometry measurement comprising densitometry data of the log;
   a 3D model generator comprising a memory storing a 3D structure representative of the log and comprising a plurality of voxels each having a respective position therein, the voxels being shaped and sized to mimic a shape of at least a portion of a potential internal feature for the respective position;
   a processing unit configured to assign a density value to each one of the voxels using the densitometry data in order to generate the 3D model of the log; and
   a display unit for displaying the 3D model,
wherein the potential internal feature is an annular feature and/or a knot, wherein the knot extends outward from the axial center line of the log,
wherein the processing unit compensates for transverse motions of the sensing of the log.

12. The system according to claim 11, wherein the densitometry measurement is obtained with an X-ray source and a detector capturing X-radiation from the X-ray source.

13. The system according to claim 12, wherein the X-ray source is a cone-beam configuration.

14. The system according to claim 12, wherein X-ray detectors are arranged over an extended area opposite the X-ray source of the log.

15. The system according to claim 11, further comprising a multi-source system of X-ray source cone-beams.

* * * * *